United States Patent [19]

Hammershaimb et al.

[11] Patent Number: 4,774,375
[45] Date of Patent: Sep. 27, 1988

[54] HF ALKYLATION AND SELECTIVE HYDROGENATION PROCESS

[75] Inventors: Harold U. Hammershaimb, Western Springs; Joel B. Spinner, Chicago, both of Ill.

[73] Assignee: UOP Inc., Des Plaines, Ill.

[21] Appl. No.: 131,886

[22] Filed: Dec. 11, 1987

[51] Int. Cl.[4] .......................... C07C 5/00; C07C 2/58
[52] U.S. Cl. .................... 585/251; 585/259; 585/331; 585/723
[58] Field of Search ............... 585/251, 259, 331, 723

[56] References Cited

U.S. PATENT DOCUMENTS

| | | | |
|---|---|---|---|
| 3,073,878 | 1/1963 | Johnson | 260/683.48 |
| 3,080,438 | 3/1963 | Sailors | 260/683.48 |
| 3,234,298 | 2/1966 | van Zijll Langhout et al. | 260/677 |
| 3,249,650 | 5/1966 | Fenske | 260/683.48 |
| 3,515,770 | 6/1970 | Tregilgas | 260/683.48 |
| 3,560,587 | 2/1971 | Borst, Jr. | 260/683.48 |
| 3,655,621 | 4/1972 | Kasperik et al. | 260/677 H |
| 3,686,354 | 8/1972 | Hervert | 260/683.43 |
| 3,696,160 | 10/1972 | Chomyn | 260/677 H |
| 3,867,473 | 2/1975 | Anderson | 260/683.45 |
| 3,925,502 | 12/1975 | Boney et al. | 260/683.48 |
| 4,139,573 | 2/1979 | Carson | 260/683.49 |
| 4,161,497 | 7/1979 | Makovec et al. | 585/714 |

OTHER PUBLICATIONS

Oil and Gas Journal, Feb. 11, 1974 issue, starting at p. 78.

Primary Examiner—Curtis R. Davis
Attorney, Agent, or Firm—Thomas K. McBride; John G. Tolonei

[57] ABSTRACT

A process using selective hydrogenation and HF alkylation in combination that employs a multifunction alkylation stripper for removal of light ends from the selective hydrogenation and a alkylation operations. The process combines the effluent from the selective hydrogenation operation, an isobutane feed stream and a bottoms stream from the HF stripper in the alkylation feed stripper. The feed stripper provides a $C_4$-plus bottoms stream that serves as the feed to the alkylation zone and a $C_3$-minus overhead that can be recovered as fuel gas. Significant benefit is obtained from this process when processing a mixed olefin feed of $C_3/C_4$ hydrocarbons and recovering a high purity $C_3$ product stream ahead of the selective hydrogenation zone. Another variation of this process allows a $C_3$ product stream to be withdrawn from the alkylation feed stripper either directly as a sidecut or downstream of an overhead condenser.

7 Claims, 1 Drawing Sheet

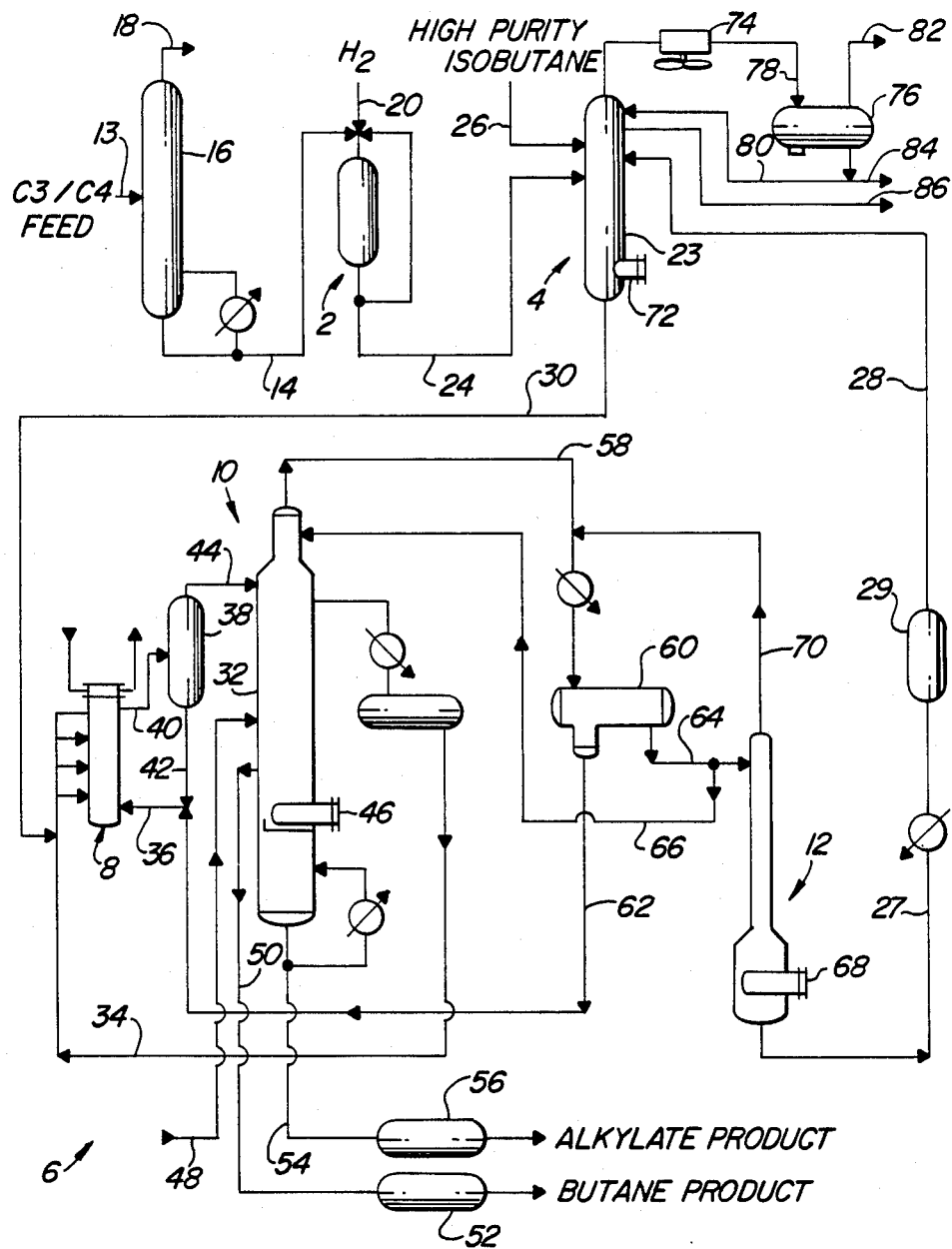

HF ALKYLATION AND SELECTIVE HYDROGENATION PROCESS

BACKGROUND OF THE INVENTION

1. Field of the Invention

This invention relates broadly to hydrocarbon processing and more specifically to the alkylation of saturated and unsaturated aliphatic hydrocarbons. The invention is directly concerned with improving the efficiency of processing olefinic and paraffinic $C_3$ to $C_5$ hydrocarbons for the recovery of high value hydrocarbon products by the fractionation, selective hydrogenation and alkylation of such feed components.

2. Prior Art Information Statement

The production of motor fuel by the alkylation of light paraffins with $C_3$ and/or $C_4$ olefins is a widely practiced commercial process. Liquid phase hydrofluoric acid (HF) is often employed as the catalyst. This process is described in U.S. Pat. Nos. 3,073,878; 3,080,438; 3,249,650; 3,515,770; 3,560,587; 3,686,354; 3,867,473; 3,925,502, 4,139,573 and 4,161,497. The process is also described in the article starting at page 78 of the Feb. 11, 1974 issue of *The Oil and Gas Journal.* These references describe process conditions, process equipment, the regeneration of the HF, and fractionation and treating procedures required in the process.

U.S. Pat. No. 3,655,621 issued to A. S. Kasperik et al. illustrates a process for the selective hydrogenation of $C_4$ diolefins in an alkylation feed stream employing a catalyst comprising presulfided nickel supported on a refractory base. In U.S. Pat. No. 3,234,298 issued to W. C. van Zijll Langhout et al., a process is disclosed for the selective hydrogenation of light, diene-containing cracked hydrocarbon oils. This process is employed to increase the stability of such materials as pyrolysis gasoline and kerosene obtained by severe thermal cracking operations. Such hydrogenation is desirable to reduce the gum-forming characteristics and other undesirable properties of these hydrocarbon mixtures. The process is described as being applicable to diene-containing hydrocarbons ranging from $C_3$ to $C_{18}$ in carbon number. The process employs a catalyst comprising sulfided nickel on alumina or sulfided molybdenum on alumina.

It is also known from U.S. Pat. No. 3,696,160 issued to K. D. Chomyn that it may be beneficial to selectively hydrogenate diolefins to monoolefins in certain hydrocarbon streams. This reference is directed to the selective conversion of propadiene and butadiene contaminants in propylene and butene charge stocks employed in alkylation processes for the production of aviation and motor fuel. In this alkylation process, a $C_3$-$C_4$ feed stream is converted to a high octane $C_7$-$C_8$ product. It is stated that a small diolefin content in the alkylation feed stream is undesirable because of increased acid consumption as a result of forming tarry acid-diolefin condensation products, which decreases the profitability of the process. The reference indicates that supported nickel and palladium catalysts are excellent hydrogenation catalysts in the diolefin conversion service, but that their tendency to deactivate in sulfur-containing feedstocks limits their utilization. The reference also discloses the use of a sulfided nickel-tungsten catalyst.

When combining a selective hydrogenation process with an HF alkylation process, it is necessary to remove light gases such as ethane, methane, and hydrogen from the hydrogenation unit effluent before it is charged to the alkylation unit. Otherwise the light ends will require venting of the HF alkylation unit with resulting HF acid losses.

In conventional flow schemes for butene alkylation, feed is derived from a depropanizer column that is also used to remove propane from an alkylation zone recycle stream. This depropanizer could be utilized to remove light gases but this would require further processing to produce a light ends free propane-propylene. In addition, a drawback to the conventional flow scheme is that to avoid fluoride contamination of the propane-propylene fraction, the entire alkylation zone recycle stream is treated to remove fluorides.

BRIEF DESCRIPTION OF THE INVENTION

It has now been discovered that the removal of these light gases can be accomplished by a multifunction alkylation stripper that receives a monoolefin feed stream from the selective hydrogenation unit, an isoparaffin feed stream for the alkylation unit, and a recycle stream from an HF stripper for the alkylation unit and separates these streams into a $C_3$-minus fuel gas product stream and a $C_4$-plus combined feed stream for the alkylation zone.

The method of this invention significantly improves the facilities for separating propane and light hydrocarbons while also providing a more efficient recycle arrangement. In this method the diolefin containing feed stream to the selective hydrogenation zone is essentially free of propane and lighter boiling products. Propane and lighter hydrocarbons are introduced into the alkylation feed stripper with the hydrogen stream to the selective hydrogenation zone, the isoparaffin feed, and the recycle stream. By returning the alkylation zone recycle to the alkylation feed stripper of this invention, $C_4$ hydrocarbons, which comprise the majority of the recycle stream, are returned to alkylation zone without treatment for fluoride removal. $C_3$-minus hydrocarbons that enter the alkylation feed stripper are recovered overhead. Although product or intermediate use of the $C_3$-minus hydrocarbons may still require treatment for fluoride removal, the greatly reduced volume of the overhead stream in comparison to the recycle stream substantially diminishes the cost of such treatment.

Accordingly in one embodiment this invention is a process for hydrofluoric acid catalyzed reaction of isoolefins and isoparaffins that utilizes selective hydrogenation of an olefin feed stream to improve the preservation of the HF acid usage. In the process of this invention, a first feed stream containing mono- and diolefins and comprising $C_4$ and heavier hydrocarbons enters a selective hydrogenation section zone together with a controlled amount of hydrogen. The selective hydrogenation zone contacts the feed stream with a selective hydrogenation catalyst at selective hydrogenation conditions to convert essentially all of the $C_4$ and $C_5$ diolefins to monoolefins. Effluent from the selective hydrogenation zone, a second feed stream comprising isobutane and a recycle stream comprising butanes and lighter hydrocarbons enter an alkylation feed stripper zone. The alkylation feed stripper separates these inputs into at least an overhead stream comprising propane and lighter hydrocarbons and a bottoms stream comprising isobutane and higher boiling hydrocarbons. The bottoms stream passes into an alkylation zone that is operated at alkylation promoting conditions and is contacted therein with an HF acid catalyst to produce an alkylation zone effluent that comprises $C_5$ and heavier branched-chain hydrocarbons, isobutane, normal butane, and propane. An isostripper column receives the alkylation zone effluent and provides an isostripper bottoms stream comprising normal butane plus $C_5$ and heavier branched-chain hydrocarbons which is withdrawn as a product and an overhead stream comprising HF catalyst, isobutane, normal butane, and propane. The isostripper overhead stream goes into an HF stripping column from which HF acid catalyst is recovered overhead and an HF stripper bottoms stream containing principally isobutane and smaller quantities of propane and normal butane is discharged and returned to the alkylation feed stripper as the beforementioned recycle.

It is, therefore, an object of this invention to improve the operation of a combination process that uses an HF alkylation zone and a selective hydrogenation zone.

It is a further object of this invention to eliminate a portion of the separation facilities necessary to operate a combined selective hydrogenation and HF alkylation process.

It is a yet further object of this invention to provide feed treatment facilities for an HF alkylation process and selective hydrogenation process that can perform multiple functions in the elimination of unwanted compounds from the feed to the HF alkylation zone.

Additional objects, embodiments, and details of the invention are set forth in the following detailed description.

BRIEF DESCRIPTION OF THE DRAWING

The FIGURE illustrates a combined operation for alkylate production. The operation includes a selective hydrogenation zone 2 that produces a monoolefinic feed, an alkylation feed stripper 4 that receives monoolefins from selective hydrogenation zone 2, along with a second isoparaffin feed stream and provides an overhead fuel gas product and a combined feed to an alkylation zone 6. The alkylation zone has a reactor 8, an isostripper 10, for recovering products from the reactor effluent, and an HF stripper 12 for recovering HF acid and delivering a recycle stream to the alkylation feed stripper 4.

DETAILED DESCRIPTION OF THE INVENTION

The detailed description of this invention is given in the context of an integrated process for the production of a $C_8$ alkylate product from a feed stream comprising $C_4$ olefins and isobutane. Presentation of the invention in a specific operational context is not meant to limit the invention to the particular details disclosed herein. In order to simplify nomenclature the term isoparaffin as used in the specification relates to the isoparaffins in the feedstock or the recycle associated with the HF alkylation reaction zone and alkylation feed stripper and does not refer to the product alkylate which is also an isoparaffin.

Referring again to the FIGURE selective hydrogenation zone 2 receives an olefinic feed through line 14. The hydrocarbon feed entering the selective hydrogen zone will consist primarily of butane, isobutane, and mixed butenes, but will also contain butadienes. In addition trace amounts of $C_3$ hydrocarbons may be present, however, the concentration of such materials should be minimized by prior recovery in order to avoid HF contamination downstream. Typical olefin containing streams from which the feed stream can be derived are available from coking, steam cracking, and fluidized catalyst cracking operations. These operations usually contain recovery facilities that can accomplish the desired removal of and recovery of the $C_3$-minus hydrocarbons from the olefinic feed stream The FIGURE shows an olefin containing feed stream of mixed $C_3$ and $C_4$ hydrocarbons from a fluidized catalytic cracking operation carried by line 13 and entering a fractionation zone comprising a depropanizer column 16. Column 16 is part of the product recovery facilities for the cracking operation. As used in this specification, the term fractionation zone refers to the process equipment in which a separation is performed and may include one or more fractionation columns as desired. Preferably, the fractionation columns are trayed columns. The fractionation zones also comprise, to the extent required, such auxiliary equipment as reboilers, overhead vapor condensors, and overhead receivers. Depropanizer column 16 separates propane and propylene from the mixed feed and withdraws these components as an overhead through line 18. Overhead 18 is usually recovered as a product stream. Bottoms from depropanizer 16 enter line 14 and provide the previously described feed to selective hydrogenation zone 2.

Selective hydrogenation is used to convert at least a substantial amount of the diolefinic hydrocarbons to monoolefinic hydrocarbons, which are the desired olefinic components of the feed while at the same time reducing the concentration of the undesired diolefinic hydrocarbons. The resulting lower concentration of diolefinic hydrocarbons in the alkylation zone results in a reduced production of by-products including oligomers which lead to the formation of deleterious compounds and fouling of the alkylation reactor. Reduction of diolefins can also produce a decrease in the consumption of the HF alkylation catalyst. Through the practice of this invention, the equipment requirements for performing the selective hydrogenation can be minimized by performing the hydrogenation step just upstream of a multifunction alkylation feed stripper. This provides a low cost and facile method of performing the hydrogenation.

In addition it is also known that the selective hydrogenation zone beneficially isomerizes butene-1 to butene-2. Butene-2 is a more desired olefin in the alkylation feed since it raises the octane of alkylate products. Therefore, selective hydrogenation has dual advantages for the alkylation zone.

The selective hydrogenation conditions employed in the hydrogenation zone are preferably similar to that maintained in upstream equipment such as depropanizer 16. Generally, the minimum pressure should be sufficient to maintain the hydrocarbon reactants in liquid phase. A broad range of suitable operating pressures, therefore, extends from about 280 (40) to about 7000 kPga (1000 psig), with a pressure between about 350 (50) and 2000 kPag (300 psig) being preferred. Reactions within hydrogenation zone favor relatively moderate temperature conditions between about 25° C. (77° F.) and 250° C. (480° F.). More preferably, the hydrogenation zone is maintained at a temperature between about 50° C. (120° F.) and about 80° C. (175° F.). The liquid hourly space velocity of the reactants through the selective hydrogenation zone should be above 1.0. Preferably, it is above 5.0 and more preferably it is between 5.0 and 35 hr.$^{-1}$. The optimum set of conditions will, of course, vary depending on such factors as the composition of the feed stream, the activity and stability of the hydrogenation catalyst, and the operating conditions of upstream and downstream equipment. Preferably, the selective hydrogenation zone 2 is operated at conditions compatible with the bottoms conditions of depropanizer 16.

In addition to olefins entering the hydrogenation zone 2, a hydrogen stream enters the zone through line 20. A significant amount of $C_3$-minus hydrocarbons, that are ultimately vented from the alkylation feed stripper, are contained in the hydrogen stream entering the selective hydrogenation zone. The concentration of $C_3$-minus hydrocarbons in the hydrogen stream may be as high as 35 mol %.

Another operating condition which may vary depending on catalyst is the ratio of hydrogen to diolefinic hydrocarbons maintained within the selective hydrogenation zone. Some catalysts, such as a palladium on alumina catalyst, require a higher hydrogen concentration to achieve the desired degree of hydrogenation. Therefore, with palladium catalysts, it may be desired to operate with a hydrogen to diolefinic hydrocarbon mole ratio of between 2:1 and 5:1. With this catalyst, it was determined that hydrogen concentrations above this range resulted in the saturation of a significant amount of monoolefinic hydrocarbons. This, of course, is undesirable as it reduces the yield of the process.

With a preferred nickel sulfide catalyst, as hereinafter described, there should be less than 2.0 times the stoichiometric amount of hydrogen required for the selective hydrogenation of the diolefinic hydrocarbons which are present in the liquid phase process stream. Preferably, the mole ratio of hydrogen to diolefinic hydrocarbons in the material entering the selective hydrogenation zone is maintained between 1:1 and 1.8:1. In some instances, it may be desirable to operate with a less than stoichiometrically required amount of hydrogen, with mole ratios down to 0.75:1 being acceptable.

The selective hydrogenation zone preferably comprises a single fixed bed reactor containing a cylindrical bed of catalyst through which the reactants move in a vertical direction. It is preferred that the reactants flow upward through the reactor as this provides good mixing. The catalyst may be present as pellets, spheres, extrudates, irregular shaped granules, etc. The prior art suggests the use of a number of metals on the selective hydrogenation catalyst including tungsten, palladium, silver, molybdenum, and nickel. Of these catalysts, it is preferred that the active catalytic metal component present in the hydrogenation catalyst is either nickel or palladium, with nickel being especially preferred. When non-noble metals are employed, the catalyst should have a high concentration or loading of the active metal, with the metal component preferably comprising over 10 wt. % of the catalytic composite. More preferably, over 20 wt. % of the catalytic composite is metallic. It is very highly preferred that the selective hydrogenation catalyst also comprises a sulfur component. The preferred catalyst may, therefore, be described as a sulfided high nickel catalyst. The preparation of catalysts of this nature is described in U.S. Pat. No. 3,919,341. The preferred selective hydrogenation catalyst has a lower sulfur concentration than the catalyst described in this reference, with sulfur levels between about 0.1 and 0.4 wt. % being preferred. The basic function of the sulfur component is believed to be the attenuation of the hydrogenation activity of the nickel. It is known in the art that carbon monoxide may be passed into a selective hydrogenation reactor for the purpose of moderating or attenuating the hydrogenation reaction. The use of carbon monoxide and other such moderators though not necessary, may be employed.

The selective hydrogenation catalyst also comprises a support or carrier material which should be relatively inert and refractory to the conditions employed within the process. The support can be formed from a variety of porous materials including various clays, diatomaceous earth, aluminas, ceramics, attapulgus clay, and other synthetically prepared or naturally occurring silicates, kaolin, kieselguhr, titania, alumina, crystalline aluminosilicates, and admixtures of two or more of these materials. The especially preferred carrier material is an alumina. Of the aluminas, gamma-alumina is preferred. The carrier material or support may have an apparent bulk density of about 0.3 to about 0.8 g/cc, a surface area of about 50 to about 550 $m^2/g$, and a pore volume of between about 0.1 and about 1.0 ml/g.

A portion of the total effluent from the selective hydrogenation zone is recycled to the hydrogenation zone inlet. This recycle is used in order to lower the concentration of diolefins and maintain liquid phase conditions when the required hydrogen would otherwise exceed the hydrogen solubility of the hydrocarbon stream.

The net effluent of the selective hydrogenation zone is a liquid phase stream similar in nature to the liquid phase process stream removed from the depropanizer but having a reduced concentration of diolefinic hydrocarbons and a corresponding increase in the concentration of monoolefinic hydrocarbons. This effluent stream is passed into zone 4 and more specifically into alkylation feed stripping column 23, which is designed and operated to remove all compounds which are more volatile than the lightest normal hydrocarbon which is desired in the charge to the alkylation section of the integrated process. These lighter materials, in this case propane and lower boiling hydrocarbons, will be concentrated into a net overhead stream which will comprise an admixture of hydrogen and light hydrocarbons. One purpose of the alkylation feed stripper is to prevent the entrance of light volatile materials into the alkylation zone where they would present operational problems. The passage of light monoolefins into the alkylation zone would also lead to the production of an increased amount of undesired side products through alkylation and polymerization reactions.

An additional feed stream rich in $C_4$ isoparaffins is charged to the alkylation feed stripper. Preferably, the isoparaffin feed stream will comprise high purity isobutane which as shown by the FIGURE, is introduced into column 23 via line 26. By high purity it is meant that this stream contains less than 20% higher boiling hydrocarbons. In its preferred form, column 23 is a multitrayed column usually containing 40-50 trays. Preferably, the temperature and pressure of column 23 will correspond with the conditions of selective hydrogenation effluent at the inlet point of line 24. Column 23 also receives a recycle stream, hereinafter described in more detail, from HF stripper 12 via a line 28. Recycle line 28 will normally contain unconverted normal paraffins and isoparaffins. In the operation depicted by the FIGURE, line 28 is rich in unconverted isobutane. When used in this specification the term rich means a stream having more than 50 mole % of the named substance.

Heavier components leave the bottoms portion of stripper zone 4 and provide a combined monoolefin, isoparaffin, and to a lesser extent paraffin, feed for the alkylation zone 10. Preferably, the combined feed comprises isobutane, normal butane, isobutene, and normal butenes which are recovered from column 23 and charged to alkylation reactor 8.

Feed entering the alkylation reactor should be dry and have a low sulfur content in order to reduce acid consumption and improve the quality of alkylate products. In addition, water causes corrosion problems in the acid environment of the alkylation unit. Methods for treating feeds for sulfur removal are well known. Standard practice for drying the feed has employed desiccant drying systems. As an alternative to the desiccant or other drying system, the alkylation feed stripper may also be used to dry the entire feed passing to the alkylation reactor. Designing the feed stripper to dry the alkylation zone requires approximately 20-25 trays between the feed withdrawal point and the lowermost wet stream inlet point. Since the column will ordinarily require approximately 20-25 trays between the inlet of line 24 and the bottoms of the column, drying capacity is easily added to the alkylation feed stripper. Therefore, the use of the alkylation feed stripper of this invention allows the elimination of drying equipment ahead of the alkylation zone.

The alkylation reaction is promoted by the presence of a mineral acid catalyst, in this case hydrofluoric acid. The acid is maintained in a liquid phase containing a minimum of water. The maximum amount of water normally allowed in the acid is about 5 wt. %. When fresh acid is charged to a plant, it is normally very dry and contains about 0.5% water or less.

Alkylation conditions in general include a pressure sufficient to maintain the hydrocarbons and acid in a liquid phase, with a general range being from about 140 kPag (20 psig) to about 3500 kPag (500 psig), and a more preferred range being from 700 kPag (100 psig) to about 1700 kPag (250 psig). It is preferred that the pressure within the reactant-catalyst contacting vessel is approximately 1050 kPag (150 psig) and essentially "floats" on the pressure maintained in downstream fractionation facilities. Although the alkylation reaction may be performed at temperatures from below $-18°$ C. $(-4°$ F.) to about 90° C. (195° F.), it is preferred to operate the commercially prevalent isoparaffin-olefin alkylation process in the range of from about 10° C. (50° F.) to about 60° C. (140° F.), with 32° C. (90° F.) being a representative and particularly preferred operating temperature.

Typically operating conditions in the alkylation zone include a high ratio of the concentration of the paraffinic or other alkylatable material to the concentration of the olefinic material in order to produce a high quality alkylate by encouraging monoalkylation instead of polymerization. A broad range for this ratio is from about 6 to about 20 with a preferred operating range being from 8 to 12. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.2:1, but it is preferred that the subject process is operated at an acid to hydrocarbon ratio of about 2:1.

There are a great number of olefin-isoparaffin alkylation processes known to those skilled in the art. The great majority of these processes will operate within the range of alkylation conditions set out above. They would, however, have substantial differences in equipment and flow paths used in performing the alkylation. These variations are attempts to obtain optimum quality alkylate by varying the method of contacting the monoolefin with the isoparaffin. Since this reaction occurs very rapidly, and also because hydrofluoric acid will catalyze the polymerization of the monoolefin, the standard alkylation method consists of first admixing acid-free streams of olefin and isoparaffin to form a reactant mixture which is then admixed with the hydrofluoric acid. In this operation, a large number of ventures or mixing nozzles are normally utilized to quickly disperse the olefin-containing stream into the acid-containing stream.

The resulting alkylation reaction is very exothermic and it is, therefore, necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the mixer settler is passed into the isostripper. This hydrocarbon phase will comprise mainly alkylate and the excess isoparaffin which was fed to the alkylation zone. Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., may be obtained by reference to the previously cited references.

The net hydrocarbonaceous effluent stream of the alkylation zone is passed into the isostripper of a recovery section. This isostripper is essentially the same as that normally associated with HF catalyst motor fuel alkylation units. The isostripper recovers the $C_8$ alkylate and other $C_5$-plus hydrocarbons as a net bottoms stream removed as the product of the process. When HF is used as the alkylation catalyst, the bottoms stream contains a small amount of isopentane produced in the alkylation zone. Some propane is also produced in the alKylation zone in this instance. Isobutane and normal butane are withdrawn from the isostripper for recycle to the alkylation zone. Normal butane may be added or withdrawn from the isostripper as necessary to maintain vapor requirements for the alkylate product. When HF is utilized as the catalyst in the alkylation zone, fluoride compounds will normally be present in these output streams. These streams should then be passed through a fluoride removal zone comprising an alumina treater and a caustic contacting zone. Isobutane is withdrawn with the overhead from the isostripper and may also be withdrawn as a sidecut from the isostripper which is returned directly to the alkylation reactor.

Overhead from the isostripper is condensed and charged to acid recovery facilities usually comprising an acid drum by an HF stripper. HF obtained from the recovery facilities is returned to the alkylation reactor while the remaining, usually isobutane rich, hydrocarbon stream from the HF stripper is charged, in accordance with this invention, to the alkylation feed stripper for light ends removal.

In the embodiment of this invention depicted by the FIGURE, alkylation feed from line 30 is combined with an isobutane rich recycle stream carried via line 34 from isostripper 32. The combined feed enters alkylation reactor 8 which comprises a shell and tube heat exchanger for circulating relatively cool water through the tube side of the exchanger thereby maintaining the reactor temperature below the desired level. HF acid catalyst enters the tube side of the reactor through a line 36. Reaction products and the commingled acid catalyst are transferred to a settler vessel 38 by line 40. Settler 38 performs a phase separation between a liquid hydrocarbon reactant and a liquid HF acid stream. Acid flows out the bottom of the settler through line 42 which supplies acid to line 36.

Alkylation reaction products and unseparated HF acid are carried overhead from settler 38 to isostripper 32 via line 44. Isostripper 32 is a trayed fractionation column having a reboiler 46 located in a lower mid portion. Proceeding down the column from the input point of line 44 unreacted isoparaffins are withdrawn and condensed for recycle to the reactor as previously mentioned via line 34. An inlet to isostripper 32 is provided next for adding saturated butanes via line 48 if required for vapor pressure requirements of the alkylate product. If normal butane needs to be removed from the process stream, it is withdrawn through line 50, caustic-treated in treater 52, and recovered as a butane product. Alkylate product empties from isostripper 32 as a bottoms stream through line 54 the contents of which receive caustic treatment in treatment zone 56 before removal from the alkylation zone. At the opposite end of isostripper 32, mixed butanes and lighter hydrocarbons are taken overhead through line 58, condensed and then collected in accumulator drum 60. A majority of the HF acid carried through line 58 drains into the boot of the accumulator drum 60. Additional HF catalyst is drained from the boot of drum 60 and carried by line 62 back to line 36 for recycle to the reactor 8. Light hydrocarbons from drum 60 pass back to isostripper 32 by line 66 to provide an overhead reflux. These light hydrocarbons are taken from a line 64. The remainder of the light hydrocarbons pass to HF stripper 12 from line 64 to further reduce their HF acid concentration.

HF stripper 12 provides a second separation of HF acid from the light hydrocarbon. A reboiler 68 provides heat to the lower section of the HF stripper for the separation. Line 70 carries HF acid overhead from the stripper and back to line 58 for removal of the HF acid from the accumulator drum and stripper circuit by the boot of accumulator drum 60. The light hydrocarbons taken from the bottom of the HF stripper by line 27 now having only a small concentration of HF acid which is on the order of 1 wt. ppm and which is further reduced by caustic treating in zone 29.

As previously mentioned, line 28 recycles unreacted butanes and lighter hydrocarbons from the alkylation section to the alkylation feed stripper. The alkylation feed stripper is designed to perform a cut between the overhead and bottoms streams at about the boiling point of propane. Therefore, the previously described isobutane-rich feed stream, taken from the bottom of the column through line 30, will usually contain some propane. The reboiler 72 controls the bottom temperature of the column and provides heat as necessary. At the upper end of the column, propane and lighter gases are taken overhead by line 78, passed through a condenser 74, and collected in a vapor drum 76. A portion of the condensed liquid returns to the column as a reflux by line 80.

All of the light gases including propane and propylene can be withdrawn from the top of the drum through a line 82 and removed from the process. Such an arrangement will be used primarily when the quantities of propane and propylene in the overhead stream are relatively small. As the quantity of propane and propylene in the overhead stream increases, it becomes desirable to recover propylene and propane as a liquid product which is taken by a line 84 from the bottom of vapor drum 76. When the quantities of propane and propylene removed by stripper 23 become relatively high, on the order of 3 wt. % of the total input to the column, a sidecut of propylene and propane may be withdrawn from the upper end of the column. The FIGURE depicts this arrangement by sidecut line 86 which withdraws a propylene and propane product from an upper tray level of column 23.

EXAMPLE

The following Example is presented to demonstrate the operation of an alkylation feed stripper designed in accordance with this invention. The Example is based on engineering calculations and operational knowledge gained from actual experience with similar processing equipment. The Example uses a process arrangement substantially the same as that shown in FIG. 1 with the exception that there is no separate recovery of propylene or propane through line 84 or 86. Product compositions in units of Kmol/hr for various lines are provided in the following Table.

Following the flow configuration and numbering system of the FIGURE, a $C_3$ and $C_4$ olefin feed having a composition given in the Table is introduced by line 13 into depropanizer column 16. Line 18 recovers a propylene/propane product stream overhead having the composition given in the Table. The remainder of the feed leaves the depropanizer column as a bottoms stream and is transferred by line 14 at a temperature of 80° C. (180° F.) and a pressure of 3100 kPag (450 psig) to the inlet of selective hydrogenation reactor 2 where it is combined with a hydrogen input stream through line 20 and a dehydrogenation recycle stream. The composition of the hydrogen input stream appears in the Table. The selective hydrogenation is carried out in the presence of a sulfided high nickel catalyst on an alumina support at a temperature of 80°–90° C. (180°–190° F.) and a pressure of 3100 kPag (450 psig). The Table lists the composition of the selective hydrogenation product which is transferred by line 24 to alkylation feed stripper 23. A high purity isobutane stream enters the alkylation stripper through line 26 and has the composition given in the Table. The recycle stream from line 28 enters a column at a temperature of 75° C. (170° F.) and a pressure of 2400 kPag (350 psig) and provides hydrocarbon inputs as listed in the Table.

The bottoms stream from the alkylation feed stripper provides the primary feed to HF alkylation zone 6. These primary feed components having the composition listed in the Table and are reacted and separated in the alkylation zone in a manner well known to those skilled in the art to provide an alkylate product recovered from isotripper 10 through line 54 and the hereinbefore described recycle stream which is taken from HF stripper 12 through line 28 and passed to feed stripper column 23.

Propane and lighter hydrocarbons are recovered overhead from column 23 through line 78 cooled in condenser 74 and collected in drum 76. Reflux requirements for column 23 are met by withdrawing condensed liquid from drum 76 and returning it to the top of column 23 by line 80. A net light gas stream is withdrawn from the top of the column through line 82 and has the composition set forth in the Table. The contents of line 82 are sent to fuel gas.

TABLE

| Line | 13 | 18 | 20 | 24 | 26 | 28 | 30 | 82 |
|---|---|---|---|---|---|---|---|---|
| $H_2$ | — | — | 6.8 | 2.3 | — | — | — | 2.3 |
| Methane | — | — | 1.4 | 1.4 | — | — | — | 1.4 |
| Ethane | — | 3.6 | 1.0 | 1.0 | — | — | — | 1.0 |
| Propylene | 272.7 | 271.8 | — | .9 | — | — | — | .9 |
| Propane | 120.4 | 116.4 | 0.2 | 4.1 | 5.3 | 12.2 | 12.2 | 9.4 |
| Isobutane | 144.7 | 3.6 | — | 141.1 | 161.2 | 73.3 | 375.6 | .05 |
| n-Butane | 62.4 | — | — | 62.4 | 8.5 | 8.6 | 79.5 | — |
| Isobutene | 76.4 | 2.7 | — | 73.7 | — | — | 73.7 | — |
| Butene-1 | 76.4 | .5 | — | 26.7 | — | — | 26.7 | — |
| Butene-2 | 132.4 | — | — | 186.9 | — | — | 186.9 | — |
| Butadiene | 4.5 | — | — | — | — | — | — | — |
| $C_5$ Hydrocarbons | — | — | — | .7 | — | .7 | .8 | — |

LB Mol/Hr

What is claimed is:

1. A process for the hydrofluoric acid-catalyzed reaction of isoolefins and isoparaffins said process comprising:
   (a) passing a first feed stream comprising hydrocarbons and containing $C_4$ and heavier diolefins in admixture with a controlled amount of a hydrogen feed stream to a selective hydrogenation reaction zone containing a selective hydrogenation catalyst and maintained at selective hydrogenation conditions to convert said $C_4$ and heavier diolefins to monoolefins;
   (b) passing the effluent from the selective hydrogenation zone, a second feed stream comprising isobutane and a recycle stream comprising butane and lighter hydrocarbons to an alkylation feed stripper zone and recovering an overhead stream comprising propane and lighter hydrocarbons and a bottoms stream comprising isobutane and heavier hydrocarbons;
   (c) passing said bottoms stream into an alkylation zone operated at alkylation-promoting conditions and contacting said bottoms stream with an HF acid catalyst to produce an alkylation zone effluent comprising $C_5$ and heavier branched chain hydrocarbons, isobutane, normal butane, propane, and HF acid;
   (d) passing the alkylation zone effluent into an isostripper zone an isostripper overhead stream comprising HF acid, isobutane, normal butane, and propane, and an isostripper bottoms stream comprising a product stream of $C_5$ and heavier branched chain hydrocarbons;
   (e) passing the isostripper overhead stream into an HF stripping column and obtaining an HF stripper overhead stream and an HF stripper bottoms stream comprising propane and isobutane; and
   (f) passing at least a portion of the HF stripper bottoms stream to said alkylation stripper zone as said recycle stream.

2. The process of claim 1 wherein the overhead stream from said alkylation feed stripper is at least partially condensed and separated to provide a fuel gas product comprising propane and lower boiling hydrocarbons.

3. The process of claim 2 wherein the partially condensed overhead is separated to provide said fuel gas product and a net liquid product.

4. The process of claim 1 wherein said selective hydrogenation catalyst comprises a nickel metal on an alumina carrier.

5. The process of claim 1 wherein said first feed stream consists essentially of $C_4$ olefins and said second stream consists essentially of isobutane.

6. The process of claim 1 wherein a propane rich sidecut stream is withdrawn from said alkylation stripper.

7. A process for the hydrofluoric acid-catalyzed reaction of isoolefins and isoparaffins said process comprising:
   (a) passing a first diolefin containing feed stream comprising $C_3$ and $C_4$ hydrocarbons into a depropanizing zone and recovering a product stream comprising $C_3$ hydrocarbons and a second feed stream comprising $C_4$ hydrocarbons;
   (b) passing said second feed stream and a controlled amount of a hydrogen feed stream to a selective hydrogenation reaction zone containing a selective hydrogenation catalyst and maintained at selective hydrogenation conditions to convert $C_4$ diolefins to monoolefins;
   (c) passing the effluent from the selective hydrogenation zone, a third feed stream comprising isobutane and a recycle stream comprising butane and lighter hydrocarbons to an alkylation feed stripper zone, and recovering an overhead stream comprising propane and lighter hydrocarbons and a bottoms stream comprising isobutane and heavier hydrocarbons;
   (d) passing said bottoms stream into an alkylation zone operated at alkylation-promoting conditions and contacting said bottoms stream with an HF acid catalyst to produce an alkylation zone effluent comprisin $C_8$ branched chain hydrocarbons, isobutane, normal butane, propane, and HF acid;
   (e) passing the alkylation zone effluent into an isostripper zone and obtaining an isostripper overhead stream comprising HF acid, isobutane, normal butane, and propane, and an isostripper bottoms stream comprising a product stream of $C_8$ branched chain hydrocarbons;
   (f) passing the isostripper overhead stream into an HF stripping column and obtaining an HF stripper overhead stream and an HF stripper bottoms stream comprising propane and isobutane;
   (g) passing at least a portion of the HF stripper bottoms stream to said alkylation stripper zone as said recycle stream.

* * * * *